United States Patent [19]

Toth

[11] Patent Number: 5,466,611
[45] Date of Patent: Nov. 14, 1995

[54] METHOD FOR THE DETERMINATION OF ANTIGENS OR ANTIBODIES IN THE PRESENCE OF AN IMMUNE COMPLEX

[75] Inventor: Tibor Toth, Marburg, Germany

[73] Assignee: Behringwerke Aktiengesellschaft, Marburg, Germany

[21] Appl. No.: 10,327

[22] Filed: Jan. 28, 1993

[30] Foreign Application Priority Data

Feb. 1, 1992 [DE] Germany ............................ 42 02 923.6

[51] Int. Cl.$^6$ ...................... G01N 33/546; G01N 33/564
[52] U.S. Cl. ...................... 436/534; 436/507; 436/509; 436/825; 436/962
[58] Field of Search ...................... 436/507, 531, 436/532, 541, 534, 509, 825; 435/962

[56] References Cited

U.S. PATENT DOCUMENTS

| | | | |
|---|---|---|---|
| 4,600,698 | 7/1986 | Toth | 436/534 |
| 4,670,381 | 6/1987 | Frickey et al. | 435/7.93 |
| 5,017,473 | 5/1991 | Wagner | 435/7.92 |

FOREIGN PATENT DOCUMENTS

| | | |
|---|---|---|
| 0068344 | 1/1983 | European Pat. Off. . |
| 0087728A1 | 9/1983 | European Pat. Off. . |
| 0290117B1 | 11/1988 | European Pat. Off. . |

OTHER PUBLICATIONS

Masson et al. "Immunoassay by Purtizle Counting" in *Manual of Clinical Laboratory Immunology* 3rd Ed. Rose et al eds. *American Society for Microbiology*, 1986 pp. 43–48.

Galvin et al. "Particle-Enhanced Immunoassays" in *Manual of Clinical Laboratory Immunology* 3rd Ed. Rose et al eds, American Society for Microbiology 1986 pp. 38–42.

Ho et al: J. Clin. Microbiology 27(5) 952–958, 1989.

Price et al; Ann Clin Biochem 20: 1–14, 1983.

Foster et al; "Turbidimetry" In Manual of Clinical Laboratory Immunology, 3rd Ed, Rose et al Eds.; American Society for Microbiology Washington D.C., 1986 pp. 25–32.

Sternberg J. C.; "Rate Nephelometry" In Manual of Clinical Laboratory Immunology 3rd Ed, Rose et al Eds; American Society for Microbiology, Washington, D.C. 1986 pp. 33–37.

Kolb et al J. Clin. Chem. Clin. Biochem 24:379–386, 1986. Interference By Rheumatoid Factor With The Detection of C-Reactive Protein By The Latex Agglutination Method, Deyo et al., The Journal Of Rheumatology 7(3):279–287 (1980).

Primary Examiner—Christine M. Nucker
Assistant Examiner—Julie Krsek-Staples
Attorney, Agent, or Firm—Finnegan, Henderson, Farabow, Garrett & Dunner

[57] ABSTRACT

The invention relates to a latex agglutination method for the detection or determination of one partner of an antigen-antibody reaction, wherein, in order to suppress non-specific reactions, to, for example, C1q and rheumatoid factors the immunochemical reaction takes place in the presence of an immune complex which does not contain any antibody or antigen that is specific for one of the partners.

20 Claims, No Drawings

METHOD FOR THE DETERMINATION OF ANTIGENS OR ANTIBODIES IN THE PRESENCE OF AN IMMUNE COMPLEX

The invention relates to an immunochemical method for the detection or determination of one partner of an antigen-antibody reaction, wherein, in order to suppress non-specific reactions, the immunochemical reaction takes place in the presence of an immune complex which does not contain any antibody or antigen that is specific for one of the partners.

It is known that specific antibodies bind to the corresponding antigens or haptens. Use is made of this reaction in many immunoassay methods. Human sera can be examined for the presence of a particular antigen, using the corresponding antibody, for example by means of nephelometry, turbidimetry, ELISA or the latex agglutination reaction. These and similar methods are well known to the person skilled in the art.

It is known that certain constituents present in the serum to be examined can interfere with these detection reactions. In particular, human serum contains the protein Clq (a complement component) and rheumatoid factors (RF). It is known that these substances can also bind to the antibody. The concentrations of rheumatoid factors and of Clq vary within very wide limits in human sera, for which reason it is normally necessary to subject the sera in advance to a treatment for inactivating Clq and/or removing endogenous rheumatoid factors. Otherwise the results and in particular the quantitative determinations can be subject to substantial error.

The detection of antigens or antibodies with the aid of the manual latex agglutination reaction has the advantage that implementation is simple and the test results are obtained in a very short time.

Because of their great precision and speed and because they lend themselves to automation, nephelometric and turbidimetric determination methods have found ready access to medical investigation laboratories.

These methods make use of the property of antigens and/or antibodies to form immune complexes with the corresponding partner in an immunochemical reaction. The formation of antigen-/antibody complexes that begins after the mixing of both the partners, and the associated change in the number and size of the light-scattering centers, can then be measured photometrically, for example.

It is known that the sensitivity of serological or immunological determination methods can be increased by the use of indicator or carrier particles that are charged with the corresponding immunological reagent (an antibody or an antigen). Red blood cells, cells of a cell culture or polymer particles can, for example, be used as carrier material. Usually, latex particles with a diameter of 0.02 to 5 µm are employed for this purpose.

Such a "particle-boosted" nephelometric or turbidimetric test can reliably detect proteins down to concentrations of some 5 ng/ml. In a particle-boosted test of this type, antibodies or antigens ("solid phase") that are bound to particulate polymers are employed. For determination of an antigen a solid-phase-bound antibody is employed, for determination of an antibody a solid-phase-bound antigen. In both cases an agglutination of the polymer particles occurs as the result of the immune reaction. This results in an increase in the size of the agglutinates and a concomitant change in the scattered light signal or in the turbidity of the reaction mixture.

EP 0 087 728 and EP 0 290 117 disclose latex agglutination methods that make use of antisera and/or gamma globulins without antibody specificity with regard to one of the reactants participating in the reaction for preventing nonspecific reactions.

Suitable antisera of this type are animal gamma globulins or heat-aggregated human gamma globulins, for example a mammalian anti-sheep erythrocyte serum and preferably a rabbit anti-sheep erythrocyte serum. Gamma globulins in the abovementioned sense are also gamma globulin fractions which can be prepared by means of known methods such as ammonium sulfate precipitation, ion exchange chromatography or immunoadsorption chromatography.

A disadvantage in this method is that the gamma globulin solutions that are used normally have to be from the same animal species as the latex-particle-bound specific detection antibodies against the antigen to be determined. Thus, for example, in the determination of myoglobin, rabbit antibodies against human myoglobin are used and the absorption solution also contains rabbit gamma globulin (immunized with sheep erythrocytes (amboceptor)). This absorption solution cannot be used in a latex agglutination test for detecting CRP, in which the antibodies, for example against human CRP, are derived from sheep, since the amboceptor is of rabbit origin and causes a spontaneous agglutination of the latex particles.

It is possible, as described in EP 0 087 728, to eliminate the interference by rheumatoid factors in the determination of CRP with sheep anti-human IgG. If the solid-phase-bound detection antibodies against human CRP are of sheep origin, however, then the human IgG present in the serum reacts in diluted sera with the (sheep) anti-human IgG with agglutination, if the level of human IgG is in about the region of equivalence (to the added anti-human IgG).

It has now been found, surprisingly, that the difficulties described above, that are caused by nonspecific agglutination, can be prevented if the agglutination reaction is carried out in the presence of an immune complex whose components do not react either with the antigen or antibody to be determined, or with the partner bound to the latex particles.

The invention thus relates to a method for the detection and or the determination of one partner (analyte) of an immunological reaction in a sample of biological material, wherein the specific immunochemical reaction takes place in the presence of an immune complex which does not contain any antibodies/antigens that are specific for one of the partners.

A preferred method is as described above, wherein the immune complex is added to the sample before addition of the detecting partner of the immunological reaction.

Preferably the addition of the immune complex takes place within a period of less than 10 minutes before the addition of the detecting partner. The immune complex can also be preincubated with the detecting partner or added together with it to the sample.

Another preferred method is as described above, wherein the immune complex contains antibodies from immunized animals that are directed against an antigen which is not the analyte. In this context the antigen can be of human, animal or vegetable origin.

Preferably the antibody : antigen ratio in the immune complex is 1:0.5 . 1:5, very preferably about 1:1.

The invention further relates to a process for the preparation of the immune complexes used in the method. Since a precipitating agent such as polyethylene glycol (PEG) is normally used in the particle-boosted agglutination method, the complexes must not be precipitated by the precipitating agent. Furthermore, they must be stable in storage for a relatively long period of time, that is to say as a rule at least 3 months, preferably at least 12 months.

Immune complexes within the meaning of the invention are all immune complexes that can be obtained according to known methods, that is by mixing solutions of the antigen with the antibody. Instead of the complete gamma globulin their $F_c$ fragments can also be used in each case. The antibodies that are used can be polyclonal (antisera) or else monoclonal. Examples which are mentioned are complexes comprising anti-human IgG from the sheep/IgG, anti-human IgM from the rabbit/IgM, antibody against rabbit gamma globulin from the goat/rabbit gamma globulin, antibody against bovine casein from the rabbit/casein, antibody against soya protein from the rabbit/soya protein.

Particularly suitable are complexes comprising antibodies against bovine gamma globulin from the rabbit/bovine gamma globulin, anti-human IgG from the sheep/IgG and anti-human IgG $F_c$ from the rabbit/IgG $F_c$. Preparation is carried out in an aqueous solution, preferably in the presence of a polar solvent that is readily miscible with water, such as dimethyl sulfoxide or dimethylformamide.

The complexes are preferably prepared in the presence of a cyclic amide, pyrrolidone (γ-amino-butyrolactam) being particularly suitable. Preferably the amide is used at a concentration of 1 to 50 percent by volume, particularly preferably 5 to 30 percent by volume. The immune complexes thus prepared are stable on storage in aqueous solutions for at least 3, preferably at least 12 months.

The method according to the invention can be used for all reactions for the detection of immunologically active substances, which are contained in the blood (serum or plasma) of mammals, in particular of humans, and in body fluids (CSF). Examples of such immunologically active substances are serum proteins.

An important characteristic of the invention is its wide-ranging applicability.

All the latices that are suitable for the latex agglutination test can be used for the latex particles which are loaded (sensitized) with the immunologically active substances. Examples which may be mentioned are homopolymers and copolymers of styrene. Preferred latices have a particle size of 0.05 to 0.6 μm. Processes for the preparation of such particles are known to the person skilled in the art.

One partner of an immunological reaction can be attached to the particles by adsorption or by covalent bonding, and in this way "loaded". The coupling of the particles to an antigen or antibody can be carried out according to methods known to the person skilled in the art. The antibodies that are used can be both monoclonal and polyclonal antibodies.

The loading of the abovementioned latex particles with the antigens or antibodies can be carried out according to a known method. Preferably the latex is loaded with antibodies against serum proteins such as myoglobins, beta 2-microglobulin, CRP or immunoglobulin E, human hormones such as human choriomicgonadotropin, enzymes such as pancreatic lipase or animal hormones such as pregnant mare serum gonadotropin. It can then be loaded as follows: the gamma globulins are precipitated from an antiserum in the usual manner, for example with ammonium sulfate, and the gamma globulin fraction is then dialyzed and concentrated to 30–50 g/l. Pure antibody solutions can also be obtained by immunoadsorption and concentrated to 2–10 g/l. A suspension of the latex particles at a concentration of approximately 20–200 g/l, preferably approximately 100 g/l, is mixed with the antibody solution and incubated for 0.5–5 hours at a temperature of between 20° and 60° C. The portion of the antibodies that is not bound to the latex particles can be removed by centrifugation and resuspension of the solid material. For use, the reagent can be resuspended in a buffer solution, preferably glycine-NaCl buffer of pH 7–8.5, which can optionally be mixed with a protein, for example with bovine or human albumin.

Further methods are known to the person skilled in the art.

The analysis of the test results can be carried out visually, or be performed by means of an apparatus, e.g. using nephelometry or turbidimetry, or by means of particle-counting methods known per se to the person skilled in the art. If the analysis is being carried out by automated means then the immune complex is metered directly into the sample to be examined. Incubation of the sample with the immune complex can, however, also be carried out in a separate step.

The following examples illustrate the invention:

EXAMPLE 1

Preparation of the immune complex 1a) 450 ml (20 g/l) of human gamma globulin in isotonic sodium chloride solution were mixed, with vigorous stirring, with 250 ml of antiserum against human IgG from sheep, diluted with 250 ml of isotonic sodium chloride.

The solution was subsequently incubated for about 10 hours at +56° C. and after cooling was mixed with 50 ml of pyrrolidone. 2 g/l benzamidinium chloride and 1 g/l sodium azide can be added as preservatives.

1b) 450 ml (20 g/l) of human gamma globulin in isotonic sodium chloride solution were mixed, with vigorous stirring, with 400 ml of antiserum against human gamma globulin from rabbit, diluted with 100 ml of isotonic sodium chloride solution. The solution was incubated for 30 min at +56° C. and mixed with 50 ml of pyrrolidone, 2 g/l benzamidinium chloride and 1 g/l sodium azide.

Latex reagent, which was prepared according to the state of the art and which contained, as specific antibodies, antibodies against human CRP from sheep, bound to latex particles, was employed according to the invention in the following test. The sensitivity of the reagent was adjusted to about 6 mg/l using a CRP standard and this test was carried out as follows:

1 drop of undiluted human serum (50 μl) to be examined was placed on a field of a test plate and 50 μl of immune complex solution (prepared according to 1 a) comprising antiserum against human IgG/human IgG were added, followed by one drop (40 μl) of latex-CRP reagent. After mixing by means of a stirring rod, the test plate was rotated and examined for agglutination after 2 min.

The following table illustrates the reliability of the method for the determination of CRP in serum:

| Serum No. | Concentration RF IU/ml | CRP* mg/l | Latex test according to the state of the art | Invention |
|---|---|---|---|---|
| 1 | 708 | neg | + | − |
| 2 | 529 | 3.8 | + | − |
| 3 | 512 | 15.7 | + | + |
| 4 | 555 | 3.8 | + | − |
| 5 | 525 | neg | + | − |
| 6 | 425 | 4.7 | + | − |
| 7 | 612 | 4.1 | + | − |
| 8 | 831 | 4.4 | + | − |
| 9 | 2,300 | 20 | + | + |

-continued

| Serum No. | Concentration RF IU/ml | CRP* mg/l | Latex test according to the state of the art | Invention |
|---|---|---|---|---|
| 10 | <20 | 10.6 | + | + |
| 11 | <20 | 14.2 | + | + |
| 12 | <20 | 70 | + | + |
| 13 | <20 | neg | − | − |
| 14 | <20 | neg | − | − |

*determined by radial immunodiffusion

The clinically interesting limit is at 6 mg/1. As the table shows, the latex tests carried out according to the state of the art were subject to interference by rheumatoid factors (cf. Interference by Rheumatoid Factor with the Detection of C-Reactive Protein by the Latex Agglutination Method. Deyo et al., J. of Rheumatology 7, (1980) 279), while all the samples were identified correctly using the method according to the invention.

EXAMPLE 2

1) Preparation of the immune complex 15 ml (16 g/l) of human gamma globulin in 50 ml of glycine-sodium chloride solution, pH 8.2, were mixed, while stirring vigorously, with 250 ml of antiserum against human IgG from rabbit. The solution was subsequently incubated for about 5 hrs. at +56° C. and after cooling was mixed with 5 ml of pyrrolidone.

2) Latex-HCG reagent was diluted for the nephelometric measurement to about 0.05 g/l solids and treated with ultrasound. A standard serum containing 12,500 mIU/ml was employed; the standard series was automatically diluted 1:20 to 1:1280, in the apparatus, i.e. concentrations of 625 to 9.8 mIU/ml were obtained.

The sera to be determined were diluted with a phosphate-sodium chloride buffer solution. For the measurement 50 μl of patient's serum and 10 μl of the immune complex reagent (prepared from antiserum against human IgG (from rabbit)/ IgG were employed. The measurement was carried out after 12 min at room temperature in a nephelometeric (e.g. Behringwerke AG). The reference curve for the measurement of the standard serum was plotted and then used for evaluation of the patients' sera.

| Serum No. | RF content IU/ml | with immune complex reagent | | without ic reagent | |
|---|---|---|---|---|---|
| | | 1:1 | 1:20 | 1:100 | 1:20 |
| 1 | 380 | <9.8 | <195 | (977 | 737 |
| 2 | 420 | <9.8 | <195 | <977 | 608 |
| 3 | 486 | <9.8 | <195 | <977 | 1,020 |
| 4 | 580 | <9.8 | <195 | <977 | 351 |
| 5 | 604 | <9.8 | <195 | <977 | 551 |
| 6 | neg. | — | 7,260 | 8,200 | 7,920 |
| 7 | neg. | — | 16,900 | 18,020 | 17,300 |
| 8 | 280 | 18 | <195 | — | 326 |
| 9 | 496 | 80 | <195 | — | 512 |
| 10 | <18 | <9.8 | <195 | <977 | <195 |
| 11 | <18 | <9.8 | <195 | <977 | <195 |

(HCG content at serum dilution (mIU/ml))

The clinically interesting limit is at about 10 mIU/ml. Sera No. 6 and No. 7 are sera from pregnant women. As is evident from the table, sera 1 to 5, 8 and 9 show, without addition of immune complex, a false "too high" value for HCG, because of RF interference.

EXAMPLE 3

1. 63 ml (14 g/l) of human IgG $F_c$ in isotonic sodium chloride solution were mixed, while stirring vigorously, with 100 ml of anti-human IgG gamma globulin fraction from rabbit (about 50 g/l of protein). The solution was incubated for 2 hours at +56° C. and, after cooling to room temperature, was mixed with 7 ml of pyrrolidone.

2. Latex-IgM reagent was diluted for a nephelometric measurement to about 0.06 g/l solids and treated with ultrasound. A standard serum containing 960 mg/l was employed; a standard series was automatically diluted 1:100 to 1:6,400, in the apparatus i.e. concentrations of 10 to 0.16 mg/l were obtained. The sera to be determined were diluted with a phosphate-sodium chloride buffer solution. For the measurement 50 μl of patient's serum were mixed with 10 μl of an immune complex reagent. In each case readings were taken after 12 minutes.

| Serum | RF content IU/ml | IgM content (mg/l) | | |
|---|---|---|---|---|
| | | without ic | with ic reagent | RID* |
| 1 | 490 | >4,000 | 1,070 | 971 |
| 2 | 596 | 3,800 | 1,660 | 1709 |
| 3 | 660 | 3,470 | 1,570 | 1576 |
| 4 | neg. | 1,130 | 1,260 | 1152 |
| 5 | neg. | 499 | 506 | 535 |

*IgM concentration by the method of radial immunodiffusion

Sera 1–3, which are positive for rheumatoid factors, indicate, without immune complex reagent, a false "too high" value for IgM.

What is claimed is:

1. A method for the immunochemical detection of an analyte contained in a biological sample by means of a latex agglutination reaction, comprising the steps of (a) contacting said sample with an immune complex which does not contain antibodies/antigens that are specific for said analyte to eliminate interference by rheumatoid factors;

(b) incubating the mixture obtained in step (a) with at least one specific binding partner of said analyte wherein, said specific binding partner is immobilized on a latex particle; and (c) detecting the presence or absence of a complex formed between said analyte and said binding partner.

2. The method of claim 1, wherein step (a) and step (b) are performed almost simultaneously.

3. The method of claim 1, herein the immune complex contains antibodies from immunized animals that are directed against an antigen which is not the analyte.

4. The method of claim 1, wherein the antigen is a protein of human, animal or vegetable origin.

5. The method of claim 1, wherein the ratio of antibody-:antigen in the immune complex is 1:0.5 to 1:5.

6. The method of claim 1, wherein the immune complex is prepared in an aqueous solution.

7. The method of claim 1, wherein the immune complex contains up to 50% by volume of a cyclic amide.

8. The method of claim 7, wherein the cyclic amide is aminobutyrolactam.

9. A method for the immunochemical determination of an amount of an analyte contained in a biological sample by means of a latex agglutination reaction, comprising the steps of (a) contacting said sample with an immune complex which does not contain antibodies/antigens that are specific for said analyte to eliminate interference by rheumatoid factors;

(b) incubating the mixture obtained in step (a) with at least one specific binding partner of said analyte wherein, said specific binding partner is immobilized on a latex particle; and (c) determining the amount of a complex formed between said analyte and said binding partner.

10. The method of claim 9, herein step (a) and step (b) are performed almost simultaneously.

11. The method of claim 9, herein the immune complex contains antibodies from immunized animals that are directed against an antigen which is not the analyte.

12. The method of claim 9, wherein the antigen is a protein of human, animal or vegetable origin.

13. The method of claims 9, wherein the ratio of antibody:antigen in the immune complex is 1:0.5 to 1:5.

14. The method of claim 9, wherein the immune complex is prepared in an aqueous solution.

15. The method of claim 9, wherein the immune complex contains up to 50% by volume of a cyclic amide.

16. The method of claim 15, wherein the cyclic amide is aminobutyrolactam.

17. The method of claim 1, wherein said detection is performed by means of nephelometry.

18. The method of claim 1, wherein said detection is performed by means of turbidimetry.

19. The method of claim 9, wherein said detection is performed by means of nephelometry.

20. The method of claim 9, wherein said detection is performed by means of turbidimetry.

* * * * *

UNITED STATES PATENT AND TRADEMARK OFFICE
CERTIFICATE OF CORRECTION

PATENT NO. : 5,466,611
DATED : November 14, 1995
INVENTOR(S) : Tibor TOTH

It is certified that error appears in the above-indentified patent and that said Letters Patent is hereby corrected as shown below:

In the Abstract, Line 4, "reactions, to, for example, Clq and rheumatoid factors" should read --reactions to, for example, Clq and rheumatoid factor--;

Claim 10, Column 7, Line 15, "herein" should read --wherein--;

Claim 10, Column 7, Line 17, "herein" should read --wherein--;

Claim 13, Column 8, Line 3, "claims" should read --claim--.

Signed and Sealed this

Twenty-sixth Day of November 1996

Attest:

BRUCE LEHMAN

Attesting Officer · Commissioner of Patents and Trademarks